United States Patent [19]
Garrel et al.

[11] Patent Number: 4,815,975
[45] Date of Patent: Mar. 28, 1989

[54] MAGNETICALLY ANCHORED DENTAL PROSTHESIS

[76] Inventors: André Garrel, Avenue de la Clastre, Saint Clément la Riviére, Hérault; Yves Vallat, 339 avenue Paul Parguel, Montpellier, Hérault; Frédéric Bousquet, 12 Résidence du Rond-Point d'Assas, Montpellier, Hérault; Jean-Louis Verdier, Bâtiment C4, 23 avenue Saint Lazare, Montpellier, Hérault, all of France

[21] Appl. No.: 96,055

[22] Filed: Sep. 11, 1987

[30] Foreign Application Priority Data

Sep. 15, 1986 [FR] France .................................. 86 13293

[51] Int. Cl.⁴ .......................................... A61C 13/235
[52] U.S. Cl. ............................................ 433/189
[58] Field of Search .................................. 433/189

[56] References Cited

U.S. PATENT DOCUMENTS

| | | | |
|---|---|---|---|
| 3,646,676 | 3/1972 | Mitchell | 433/189 |
| 4,203,216 | 5/1980 | Deguemp | 433/189 |
| 4,431,419 | 2/1984 | Portnoy | 433/189 |

FOREIGN PATENT DOCUMENTS

| | | | |
|---|---|---|---|
| 3140464 | 4/1983 | Fed. Rep. of Germany | 433/189 |
| 2587895 | 4/1987 | France | 433/189 |

Primary Examiner—John J. Wilson
Attorney, Agent, or Firm—Herbert Dubno; Andrew Wilford

[57] ABSTRACT

A removable dental prosthesis is magnetically secured to an anchor face of a ferromagnetic body implanted in a jaw by an attachment system comprising a saliva-resistant cushioning mass secured in the prosthesis and forming a pocket open toward the anchor face, a ferromagnetic and saliva-resistant shell seated in the pocket and open toward the face, a permanent magnet fixed in the shell and having a magnet face confronting the anchor face, and a permanently magnetized plate having a rear face directly contacting the magnet face, a front face directly confronting the anchor face, and an outer periphery. The plate is of a material not corrosible by saliva and is magnetically polarized like the magnet which itself is of relatively great strength and of a material corrosible by saliva. The outer periphery of the plate is sealed to the shell so as to encapsulate the magnet in the shell with the plate and thereby protect it from corrosion. With this system the flux of the magnet passes substantially entirely via the plate to the anchor body when the front and anchor plates are closely juxtaposed.

10 Claims, 4 Drawing Sheets

MAGNETICALLY ANCHORED DENTAL PROSTHESIS

FIELD OF THE INVENTION

The present invention relates to a dental prosthesis. More particularly this invention concerns a prosthesis that is anchored to the mandible by means of magnets.

BACKGROUND OF THE INVENTION

It is known, for example from French Pat. No. 2,587,895, to secure a removable dental prosthesis magnetically to an anchor face of a ferromagnetic body implanted in a jaw by means of an attachment system comprising a saliva-resistant cushioning mass secured in the prosthesis and forming a pocket open toward the anchor face, a ferromagnetic and saliva-resistant shell seated in the pocket and open toward the face, and a permanent magnet fixed in the shell and having a magnet face confronting the anchor face. The permanent magnet is of relatively great strength and of a material corrosible by saliva.

The shell typically leaves the magnet face exposed and, in order to protect it, it is covered with a layer about 3 mm thick of a protective material such as an acrylic resin. As this material is not magnetically attractable, it forms in effect an air gap between the magnet face and the anchor face. The magnetic attraction is therefore severely limited, so that the practice is to reduce the thickness of the protective coating in order to obtain maximum hold. This of course leaves the magnet relatively poorly protected and, if a leak occurs, the magnet quickly corrodes so that the denture needs to be repaired or replaced.

OBJECTS OF THE INVENTION

It is therefore an object of the present invention to provide an improved magnetic attachment system for a dental prosthesis.

Another object is the provision of such a magnetic attachment system for a dental prosthesis which overcomes the above-given disadvantages, that is which holds well while having a long service long as a result of its magnet being well protected.

SUMMARY OF THE INVENTION

According to this invention a removable dental prosthesis is magnetically secured to an anchor face of a ferromagnetic body implanted in a jaw by an attachment system comprising a saliva-resistant cushioning mass secured in the prosthesis and forming a pocket open toward the anchor face, a ferromagnetic and saliva-resistant shell seated in the pocket and open toward the face, a permanent magnet fixed in the shell and having a magnet face confronting the anchor face, and a permanently magnetized plate having a rear face directly contacting the magnet face, a front face directly confronting the anchor face, and an outer periphery. The plate is of a material not corrosible by saliva and is magnetically polarized like the magnet which itself is of relatively great strength and of a material corrosible by saliva. The outer periphery of the plate is sealed to the shell so as to encapsulate the magnet in the shell with the plate and thereby protect it from corrosion. With this system the flux of the magnet passes substantially entirely via the plate to the anchor body when the front and anchor plates are closely juxtaposed.

Thus with the system of this invention even though the magnet is well protected, the element doing the protecting is a relatively weak permanent magnet that serves to channel the magnetic flux directly to the anchor face, which typically engages the front face of the plate flatly and in direct contact. Hold is excellent and the magnet can be counted on not to be corroded as it is very well protected.

According to another feature of this invention the plate is mainly flat and its outer periphery is generally circular. In addition the seal is formed by a metal-to-metal solder joint at the outer periphery. The seal can be at a joint that is recessed in the cushioning mass.

In accordance with this invention the plate has an annular rim projecting back from the front face around the magnet. The shell has a lip engaging over the outer periphery of the plate forwardly thereof. This lip either can be bent over so that the shell is cup-shaped or it can be part of an L-section sleeve in which case the shell has a separable back plate rearwardly closing it.

Normally according to this invention the pocket, shell, magnet, and plate are generally centered on an axis and the magnet and plate are identically axially polarized. In addition the shell and plate are of a high-chromium steel.

DESCRIPTION OF THE DRAWING

The above and other objects, features, and advantages will become more apparent from the following, it being understood that any feature described with reference to one embodiment of the invention can be used where possible with any other embodiment and that reference numerals not specifically mentioned with reference to one figure but identical to those of another refer to structure that is functionally if not structurally identical. In the accompanying drawing.

SPECIFIC DESCRIPTION

Figure 1:
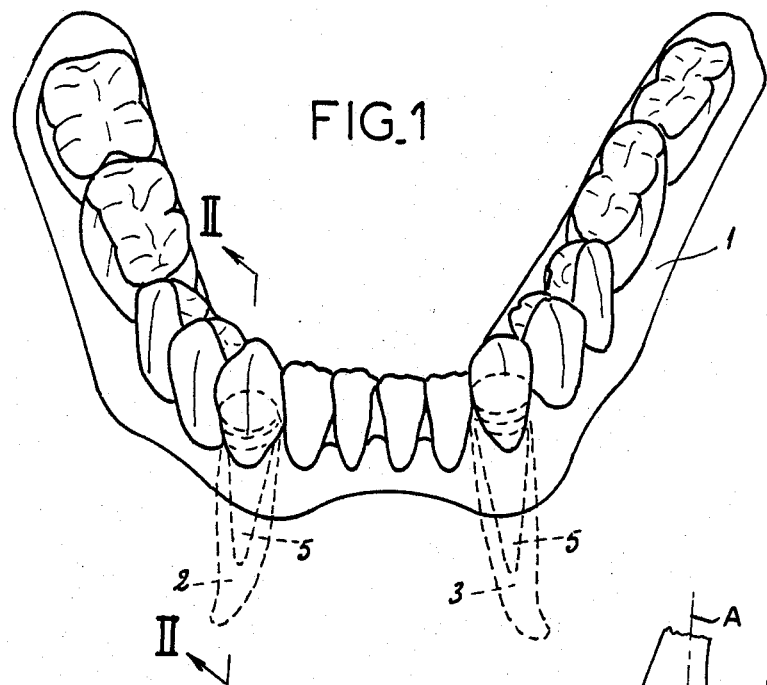
FIG. 1 is a partly diagrammatic perspective view of a dental prosthesis according to this invention.
Figure 2:
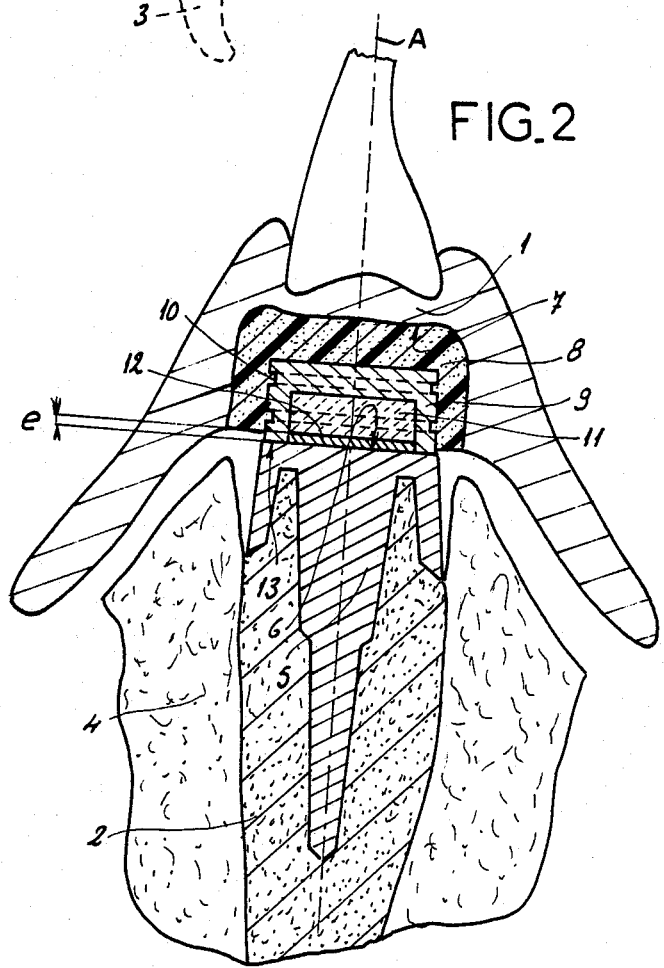
FIG. 2 is a large-scale section taken along line II—II of FIG. 1.

As seen in FIGS. 1 and 2 a dental prosthesis 1, here a full set of false lower teeth, is secured in place on the roots 2 and 3 remaining from the two outer canines. The canine root 2 shown in FIG. 2, which is substantially identical to the root 3, is provided with a ferromagnetic body 5 having a central stem projecting down into and cemented in place in the root 2 and a skirt engaging down over the top of the root 2. This body 5 has a planar and normally circular top surface 6 slightly above the level of the adjacent gums. A high-chromium ferromagnetic stainless steel having 12% to 22% by weight of chromium, for example F17 steel having 17% by weight of chromium, 82.9% iron, and 0.06% carbon is used for the body 5.

In addition as best shown in FIG. 2 the prosthesis 1 is provided across from the root 2 (and also across from the root 3 although this is not illustrated) with a recess 7 of basically blind cylindrical shape open toward the body 5. This recess 7 is provided with a cup-shaped body 8 of a biologically inert substance like silicone that is reasonably elastic and that serves here as a cushion. A cup 9 of the same ferromagnetic material as the body 5 fits complementarily in the cushion 8, and in fact is formed with outwardly open grooves 10 into which the material of this cushion 8 enters in order to anchor it solidly in the denture 1. The cup 9 is of downwardly open cylindrical shape and centered on an upright axis A that is also the rotation-symmetry axis of the cushion 8.

Inside the cup 9 is a short cylindrical permanent magnet 11 polarized axially and formed of magnetic particles imbedded in a synthetic-resin binder. Such a magnet 11 is quite powerful but is regrettably sensitive to attack by the acids in saliva. The lower surface of this magnet 11 is spaced axially somewhat back from the plane of the rim of the cup 9.

Figure 3:
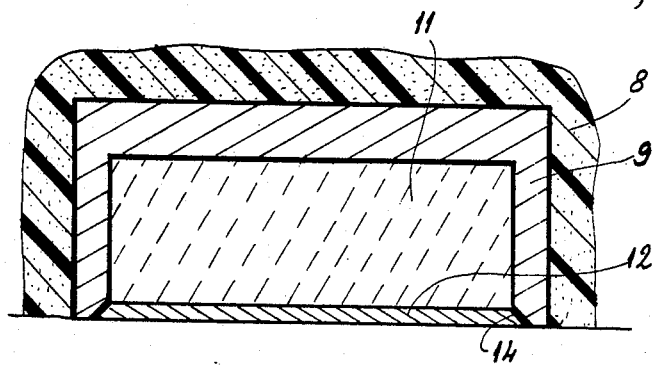
FIGS. 3 through 14 are large-scale sectional views corresponding to a detail of FIG. 2 showing different anchoring systems in accordance with the invention.

According to this invention the lower face of the magnet 11 is covered by a disk 12 of saliva-resistant magnetic material. This disk 12 is formed of a magnetic steel containing substantial chromium and cobalt. This disk 12, while not being as strong a permanent magnet as the magnet 11, is axially polarized like this magnet 11 and is hermetically secured as shown in FIG. 3 by a weld joint 14 to the inner periphery of the rim of the cup 9. Thus according to this invention the corrosible core magnet 11 is protected by this disk 12 from direct contact with any liquids in the mouth. When the disk 12 and rim of the cup 9 are seated atop the surface 6 with the axis A perpendicular thereto virtually all of the magnetic flux from the magnet 11 will be channeled through the disk 12 to the magnetically attractable body 5. The thickness e of the disk 12 is about 0.2 mm, but since this disk 12 is itself magnetic this spacing of the magnet 11 from the body 5 is virtually irrelevant. The result is therefore excellent holding power.

The weld 14 can be made as a pure metal-to-metal weld, done for example by laser to avoid heating the magnet 11 above the Curie point and reducing its powder. This joint 14 could also be made by means of a dental cement or a cold-acting metal-to-metal adhesive or solder.

Figure 4:
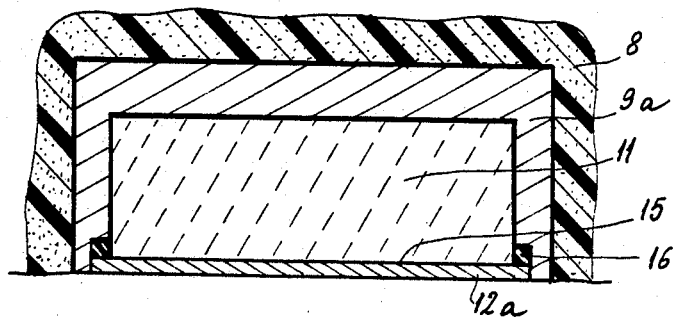
Figure 5:
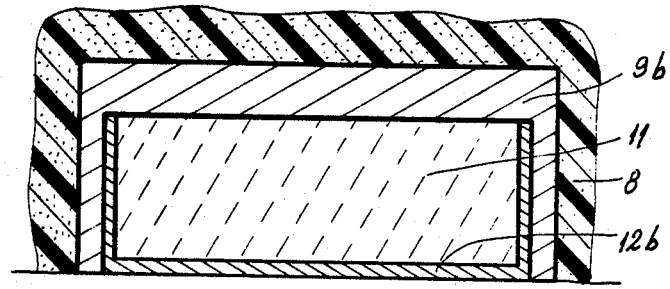

In the arrangement of FIG. 4 the disk 12a is of larger diameter than the disk 12 and has a planar rear face 15 that sits atop an elastomeric seal ring 16 itself sitting on a shoulder in the rim of the cup 9a. Normally, as in FIGS. 1 and 2, no adhesive or the like is provided between this rear face and the front face of the magnet 11 so that same contact each other directly. An added benefit of doing this is that the magnet 11, which is firmly anchored in the cup 9a, will serve to hold the disk 12 or 12a in place just by magnetic attraction FIG. 5 shows a cup-shaped disk 12b reaching back in the cup 9b all around the magnet 11, which in this case is diametrally somewhat smaller than the interior of the cup 9b. This arrangement is particularly easy to mass produce.

Figure 6:
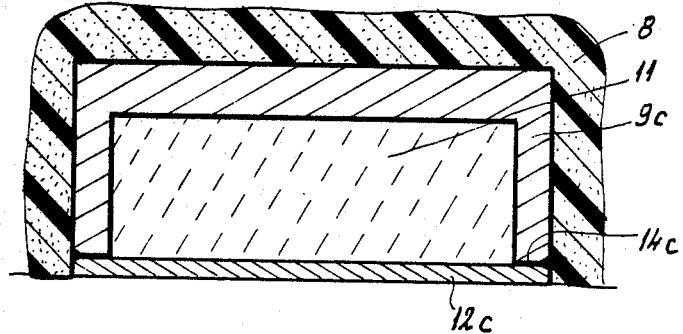

In FIG. 6 the disk 12c is of the same diameter as the cup 9c and same is somewhat shorter than in any of the above-discussed embodiments. This disk 12c sits via a solder or adhesive joint 14c on the edge of the rim of the cup 9c. Thus with this arrangement the joint 14c, which is typically somewhat more sensitive to attack by saliva than the disk 12c and the cup 9c, is recessed in the synthetic-resin cushion 8 and, therefore, fairly well protected itself.

Figure 7:
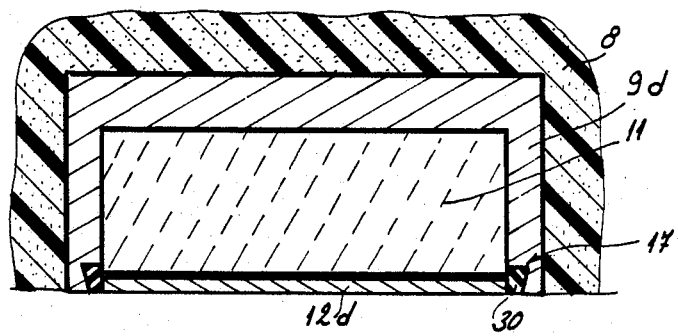

The disk 12d of FIG. 7 fits within the cup 9d and is adhered to the face of the magnet 11. The cup 9d is formed with a radially inwardly and axially outwardly open groove 17 measuring radially about 3 mm deep and axially about 3 mm wide and this groove 17 is filled with an acrylic-resin seal ring 30 that bears against the outer edge of the disk 12d.

Figure 8:
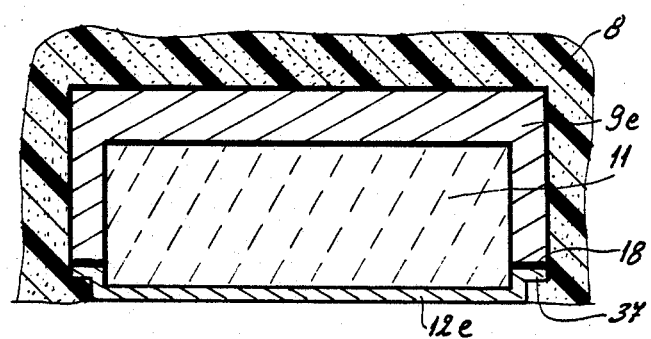

FIG. 8 shows a disk 12e whose outer periphery 37 is stepped axially back and adhered by a weld or adhesive ring 18 to the similarly recessed face of the rim of the cup 9e. The cushion 8 here extends forward and radially inward past this edge 37 to protect the ring 18 and hold the entire capsule thus formed in place.

Figure 9:
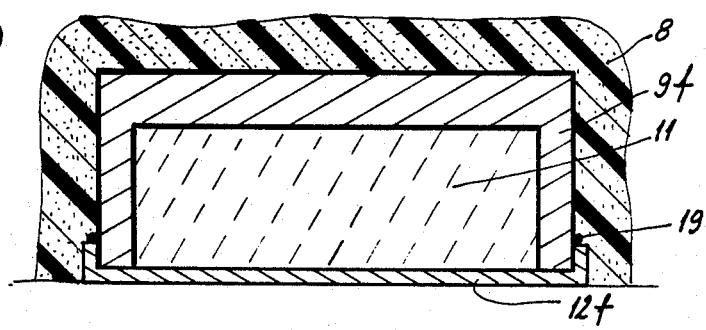

The system of FIG. 9 uses a cup-shaped disk 12f which, unlike the disk 12b of FIG. 5, is large enough to reach completely around and past the rim of the cup 9f. The axially backwardly projecting rim is secured by adhesive 19 which, once again, is protected by the material of the cushion 8.

Figure 10:
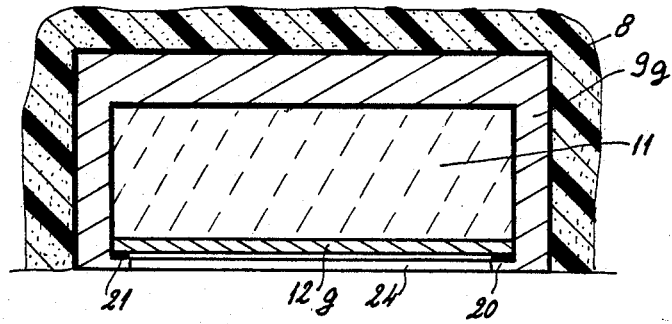

The cup 9g of FIG. 10 has an outer edge that is bent back at 20 to reach forward past the disk 12g. This creates a small gap 24. The disk 12g is secured at the forward side of its outer periphery at 21 via an adhesive to the back edge of the bent-in lip 20.

Figure 11:
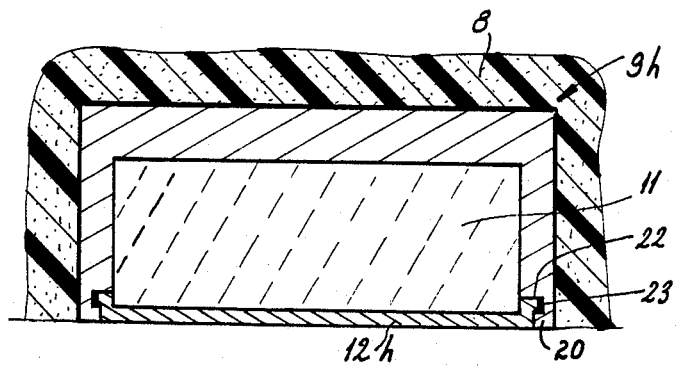

To avoid creating this gap 24, it is possible as shown in FIG. 11 to use a disk 12h having a stepped-back rim 22 as in FIG. 8. It is held in place in the cup 9h by a gasket or seal ring 23 around its edge and held in place by the bent-over lip 20.

Figure 12:
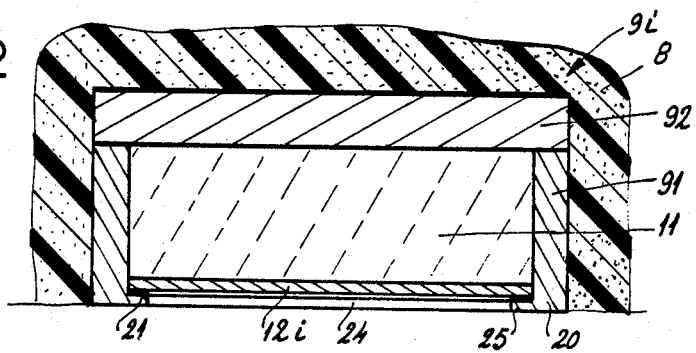

A construction similar to that of FIG. 10 is achieved in FIG. 12 without deforming the cup 9i by forming same of a sleeve 91 and a rear end cap 92. Thus this arrangement can be assembles simply by dropping the disk 12i and then the magnet 11 and ring 21 in place, and then fitting on the rear plate 92. The joint between the plate 92 and rim 91 of the cup 9i is so deeply buried that it is not a potential leakage site.

Figure 13:
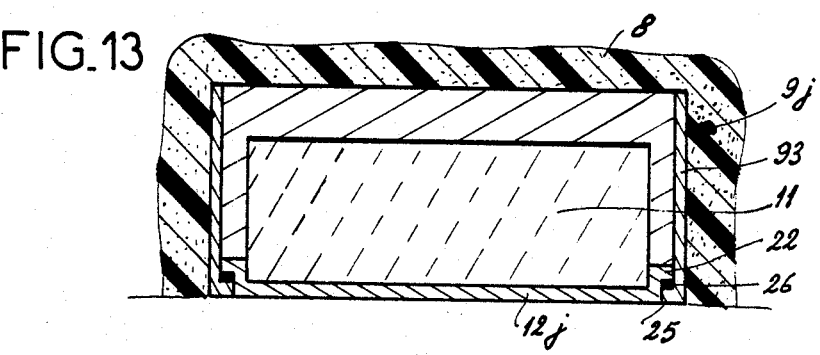
Figure 14:
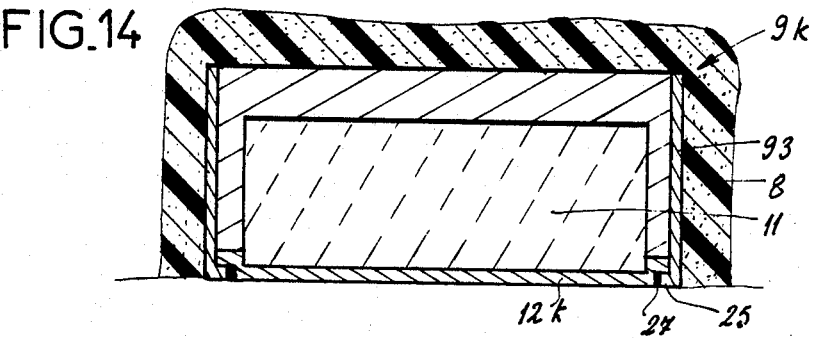

Yet another easy-to-make system is seen in FIG. 13. Here a disk 12j shaped like the disks 12h and 12e with a stepped-back outer periphery 22 is held in place on a cup 9j by means of an L-section ring 93 whose lip 25 engages via a seal ring 26 over the stepped-out edge 22. FIG. 14 shows a variation on this system with a seal ring 27 compressed radially rather than axially between the disk 12k and a sleeve 93 fitting around a cup 9k. Unlike the system of FIG. 12, these arrangements both eliminate any gap 24 so that the face 6 of the body 5 need not be raised and/or so that best magnetic conduction is obtained.

We claim:

1. In a removable dental prosthesis magnetically secured to an anchor face of a ferromagnetic body implanted in a jaw, an attachment system comprising:
    a saliva-resistant cushioning mass secured in the prosthesis and forming a pocket open toward the anchor face;
    a ferromagnetic and saliva-resistant shell seated in the pocket and open toward the face;
    a permanent magnet fixed in the shell and having a magnet face confronting the anchor face, the permanent magnet being of relatively great strength and of a material corrosible by saliva;
    a permanently magnetized plate having a rear face directly contacting the magnet face, a front face directly confronting the anchor face, and an outer periphery, the plate being of a material not corrosible by saliva, the plate being magnetically polarized like the magnet; and
    means for sealing the outer periphery to the shell for encapsulating the magnet in the shell with the plate and thereby protecting it from corrosion, the flux of the magnet passing substantially entirely via the plate to the anchor body when the front and anchor plates are closely juxtaposed.

2. The prosthesis-attachment system of claim 1 wherein the plate is mainly flat and its outer periphery is generally circular.

3. The prosthesis-attachment system of claim 1 wherein the means includes a metal-to-metal solder joint at the outer periphery.

4. The prosthesis-attachment system of claim 1 wherein the means includes a joint that is recessed in the cushioning mass.

5. The prosthesis-attachment system of claim 1 wherein the plate has an annular rim projecting back from the front face around the magnet.

6. The prosthesis-attachment system of claim 1 wherein the shell has a lip engaging over the outer periphery of the plate forwardly thereof.

7. The prosthesis-attachment system of claim 6 wherein the lip is bent over and the shell is cup-shaped.

8. The prosthesis-attachment system of claim 6 wherein the shell has a separable back plate rearwardly closing it.

9. The prosthesis-attachment system of claim 1 wherein the pocket, shell, magnet, and plate are generally centered on an axis and the magnet and plate are identically axially polarized.

10. The prosthesis-attachment system of claim 1 wherein the shell and plate are of a high-chromium steel.

* * * * *